United States Patent
Williams et al.

(10) Patent No.: US 8,283,483 B2
(45) Date of Patent: * Oct. 9, 2012

(54) TRIGLYCERIDE MACROMONOMERS

(75) Inventors: Neal St. John Williams, Warfield (GB);
Chris Lampard, Slough (GB)

(73) Assignee: Akzo Nobel Coatings International B.V., Arnhem (NL)

( * ) Notice: Subject to any disclaimer, the term of this patent is extended or adjusted under 35 U.S.C. 154(b) by 266 days.

This patent is subject to a terminal disclaimer.

(21) Appl. No.: 12/808,954

(22) PCT Filed: Dec. 16, 2008

(86) PCT No.: PCT/EP2008/067577
§ 371 (c)(1),
(2), (4) Date: Jul. 15, 2010

(87) PCT Pub. No.: WO2009/077513
PCT Pub. Date: Jun. 25, 2009

(65) Prior Publication Data
US 2011/0009523 A1    Jan. 13, 2011

(30) Foreign Application Priority Data
Dec. 19, 2007  (GB) .................................. 0724720.8

(51) Int. Cl.
*C11C 3/00* (2006.01)
*C07C 51/353* (2006.01)
*C08F 22/10* (2006.01)

(52) U.S. Cl. ........ 554/173; 554/227; 524/559; 524/832; 523/122

(58) Field of Classification Search ................ 524/559, 524/832; 523/122; 554/173, 227
See application file for complete search history.

(56) References Cited

U.S. PATENT DOCUMENTS

| 5,719,301 A | 2/1998 | Sleeter |
| 6,121,398 A | 9/2000 | Wool et al. |
| 6,646,085 B1 | 11/2003 | Craun et al. |
| 2005/0203246 A1 | 9/2005 | Thames et al. |

FOREIGN PATENT DOCUMENTS

| DE | 39 38 149 A1 | 5/1991 |
| WO | WO 99/21900 A | 5/1999 |

OTHER PUBLICATIONS

International Search Report, PCT/EP2008/067579, mailed Apr. 29, 2009, 3 pages.
Written Opinion of International Searching Authority, PCT/EP2008/067579, mailed Apr. 29, 2009, 6 pages.
Reply to Written Opinion of International Searching Authority, PCT/EP2008/067579, dated Sep. 30, 2009, 3 pages.
International Preliminary Report on Patentability, PCT/EP2008/067579, completed on Mar. 29, 2010.

(Continued)

*Primary Examiner* — David W Wu
*Assistant Examiner* — Vu A Nguyen
(74) *Attorney, Agent, or Firm* — Kenyon & Kenyon LLP

(57) ABSTRACT

A polymerisable ethylenically unsaturated macromonomer being the reaction product of: i) an adduct formed from the reaction of an unsaturated non-mineral oil reacted with an enophile having an acid, ester or anhydride moiety and ii) an ethylenically unsaturated monomer having a moiety reactive with the acid, ester or anhydride moiety of the enophile and iii) a chain extender material having at least two moieties reactive with the acid, ester or anhydride moiety of the enophile.

20 Claims, 2 Drawing Sheets

OTHER PUBLICATIONS

Figure 1:
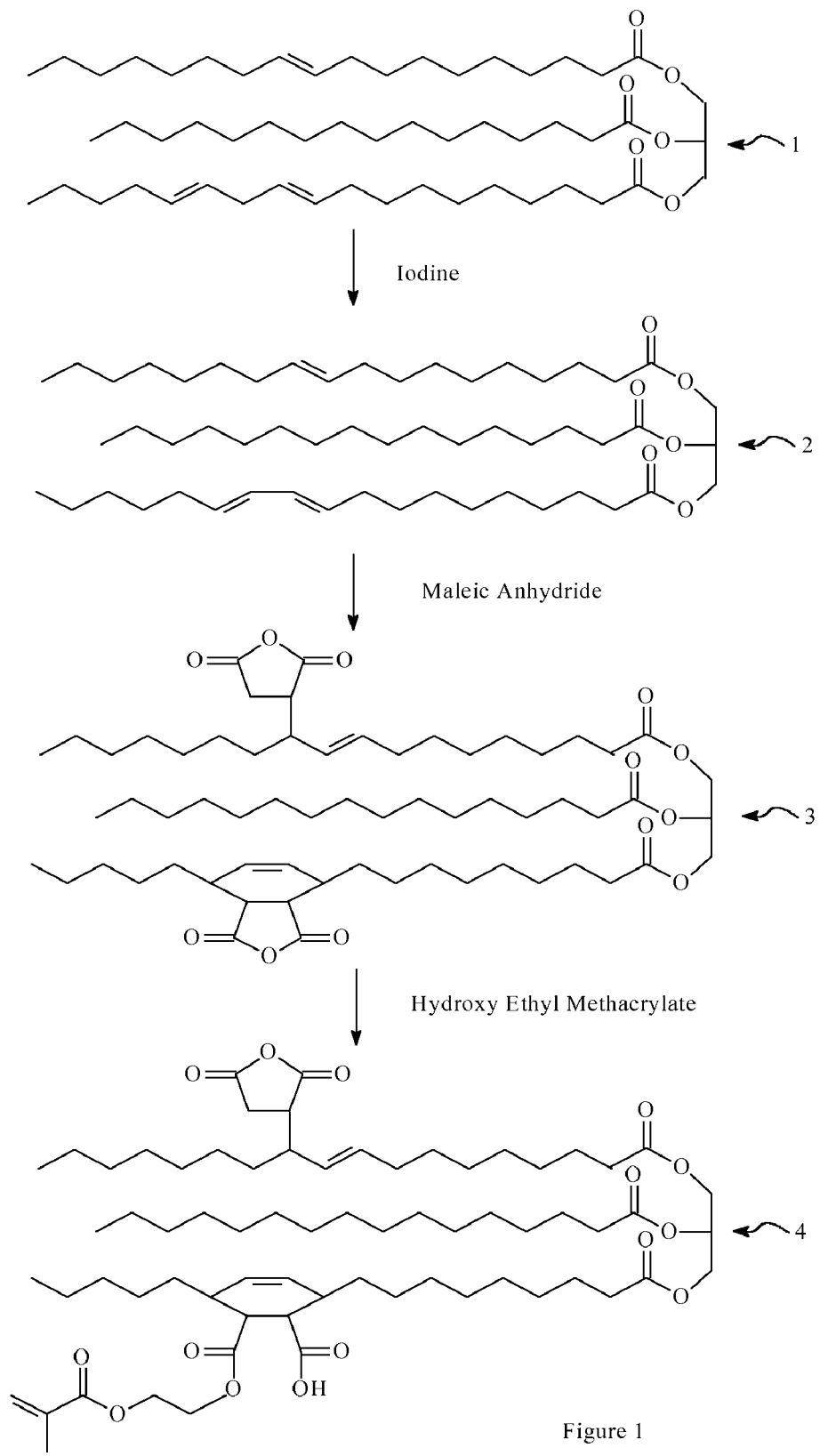

International Search Report, PCT/EP2008/067578, mailed Apr. 21, 2009, 3 pages.

Gultekin, M. et al., "Styrenation of castor oil and linseed oil by macromer method," Macromol. Mater. Eng., vol. 283, 2000, pp. 15-20 (XP002522953).

International Search Report, PCT/EP2008/067577, mailed Apr. 24, 2009, 2 pages.

TRIGLYCERIDE MACROMONOMERS

REFERENCE TO RELATED APPLICATIONS

This application is the U.S. National Phase of PCT/EP2008/067577 filed on Dec. 16, 2008, and claims the benefit of GB Application No. 0724720.8, filed on Dec. 19, 2007.

This invention relates to ethylenically unsaturated macromonomers derived from unsaturated non-mineral oils—especially plant and vegetable oils; polymers—particularly in the form of aqueous dispersions derived from them and finally adhesives, coatings, especially architectural coatings, comprising the polymers.

By architectural coatings is meant paints, varnishes and woodstains, especially for use on the interior and exterior of structures and buildings such as houses, and also coatings for use in the garden such as fence paints and also metal used on railings.

There is increasing awareness of the need to use renewable resources in industry.

For many years, the main feedstock for industry, especially the chemical industry, has been fossil feedstock, either in the form of petroleum or coal. Whilst economists, mining and oil exploration experts may argue about the lifetime of known and yet to be discovered fossil feedstock reserves, it is indisputable that, in time, those reserves will inevitably be exhausted and even prior to that, become too expensive to be of any use as a feedstock in all but the most specialised applications.

Furthermore, converting this fossil feedstock into useful material for industry requires energy, releasing carbon dioxide and contributing to global warming. In addition, at the end of the useful life of the material, still more carbon dioxide is released, further adding to global warming.

Coatings typically comprise a mixture of particulate inorganic material and organic material. The inorganic material is usually a mixture of pigments and fillers and/or extenders. The pigments give colour to the paint and the fillers and extenders provide other properties, such as hardness, to the paint film. The organic material largely comprises a binder, the role of which, as the name suggests, is to bind any particulate matter together. It also provides adhesion to the surface to which the coating is applied.

The binders are usually high molecular weight polymers derived from monomers obtained by refining and further processing of fossil feedstock. The polymers are often produced in the form of aqueous dispersions of polymer microparticles referred to as latex. For simplicity it should be understood that the term polymer is used here to include homopolymers, copolymers, terpolymers and so on.

The manufacture and use of such polymer binders consumes some of the worlds non-renewable resources and in the process produces carbon dioxide.

Thus there is a need for polymer binders that are based, at least in part, on renewable feedstock such as that obtained from plant and/or animal material.

Oils are such a natural and renewable feedstock obtainable from various plants and animals, including fish. In the case of plants, it is generally the fruit that yields the oil. The term oil as used here, excludes mineral oils obtained form fossil feedstock such as petroleum and coal.

These oils are largely composed of a mixture of triglycerides (ie tri-esters of glycerol) characterised by the fatty acids portion. For example, the fatty acids component of the triglycerides making up palm oil, linseed oil and soya oil are shown below and have the following approximate composition by weight %:

|  | Palm oil | Linseed oil | Soya oil |
|---|---|---|---|
| Palmitic acid ($C_{16}$, 0) | 44 | 6 | 10 |
| Stearic acid ($C_{18}$, 0) | 4.5 | 2.5 | 4 |
| Arachidic ($C_{20}$, 0) | 0 | 0.5 | 0 |
| Oleic acid ($C_{18}$, 1) | 40 | 19 | 23 |
| Linoleic ($C_{18}$, 2) | 10 | 24.1 | 51 |
| Linolenic ($C_{18}$, 3) | 0 | 47.4 | 7 |
| Other | 1.5 | 0.5 | 5 |
| Saturated | 48.5 | 9 | 14 |
| Unsaturated (total) | 50.0 | 90.5 | 81 |
| Unsaturated (>1) | 10.0 | 71.5 | 58 |
| Iodine value | 44-54 | 155-205 | 120-141 |

The subscript refers to the carbon chain length of the fatty acid and 0, 1 or 2 indicates the number of ethylenically unsaturated bonds in the fatty acid.

Such unsaturated oils can be classified as drying, non-drying or semi-drying oils. What is meant by such terminology is the extent to which they autoxidise at normal temperatures to form a hard, dry film. Autoxidation is the process by which unsaturated oils absorb oxygen from the atmosphere to form in-situ hydroperoxides which then decompose to produce free radicals causing the oils to dry. The more unsaturated bonds the oil has, the more rapidly and completely it will dry. Similarly, oils with at least two unsaturated bonds per triglyceride, especially when conjugated, autoxidise even more readily. Nature, however, rarely produces conjugated unsaturation.

The extent of the unsaturation is measured by the iodine value. It is generally regarded that non-drying oils have iodine values of less than 100, semi-drying oils from 100 to 140 and drying oils over 140 g of iodine per 100 g of oil. A more extensive list of iodine values can be found on pages 34 and 35 of The Chemistry of Organic Film Formers by D. H. Solomon, published by John Wiley and Sons in 1967, which are hereby incorporated by reference.

The oils can be characterised according to the number of double bonds per triglyceride type. We have found that a typical sample of palm oil, for example, has the following distribution, expressed on a weight % basis.

| | |
|---|---|
| 5 double bonds per triglyceride | <1 |
| 4 double bonds per triglyceride | ca 10 |
| 3 double bonds per triglyceride | ca 5 to 10 |
| 2 double bonds per triglyceride | ca 35 |
| 1 double bonds per triglyceride | ca 35 to 40 |
| 0 double bonds per triglyceride | ca 10 |

Thus whilst approximately 48.5% of the fatty acids in the oil are palmitic or stearic and thus saturated, nevertheless only about 10% of the triglycerides will be composed of fatty acids where all three are saturated, and therefore free of double bonds. This saturated portion of the palm oil is unreactive to enophile and dienophiles.

US 20050203246 discloses monomer formed by reacting unsaturated vegetable oils (specifically sunflower oil, linseed oil or soya bean oil) with an enophile or dienophile having an acid, ester or anhydride functionality, to form a derivative, followed by reacting the derivative with at least a molar equivalent of suitable hydroxyl, amine, thiol, oxirane or other functional vinyl monomer to form an ethylenically unsaturated triglyceride monomer. The weight average molecular weight of such monomers is approximately 1000 Daltons. It also discloses polymer latices containing up to 6% by weight of the monomer calculated on the polymer solids However, we have found that latices derived from monomer mixtures comprising such triglyceride monomer, and paints based on them, tend to be soft. They also tend to exude oily material, which appears on the surface, over time. Furthermore, the requirement to react the derivative with a molar equivalent of the vinyl monomer means that the macromonomer is more expensive and less of the oil is incorporated into the macromonomer than otherwise.

In addition, architectural coatings using binders comprising such monomers, especially those used on interior surfaces, tend to have a yellow hue. This makes it difficult to formulate bright whites and the pastel colours.

These problems of the known prior art severely limits the utility of these known triglyceride monomers.

We have now developed a new macromonomer based on unsaturated non-mineral oils obtained from plant or animal material which can be used in much higher amounts in polymer binders and with much reduced or no exudation of oily material.

According to the present invention there is provided a polymerisable ethylencially unsaturated macromonomer being the reaction product of
i) the adduct formed from the reaction of an unsaturated non-mineral oil reacted with an enophile having an acid, ester or anhydride moiety, preferably maleic anhydride and
ii) an ethylenically unsaturated monomer having a moiety reactive with the acid, ester or anhydride moiety of the enophile and
iii) a chain extender material having at least two moieties reactive with the acid, ester or anhydride moiety of the enophile.

The macromonomer is considered to be polymerisable through the ethylenic unsaturation provided by the monomer ii) rather than through any unreacted unsaturation in the fatty acid chains of the triglycerides comprising the oil. Normally, the polymerisable ethylenic unsaturation of the macromonomer ii) is dependent from the fatty acid chain, usually indirectly, rather than exists in the backbone of the chain.

Preferably the weight average molecular weight, Mw, of the macromonomer is 1000 to 50000 Daltons, more preferably from 1500 to 40000, still more preferably from 2000 to 40000, yet more preferably from 5000 to 30000 Daltons, even more preferably from 10000 to 25000 Daltons and most preferably form 19000 to 23000 Daltons. The number average molecular, Mn is preferably from 1000 to 5000 Daltons, more preferably from 1000 to 4000, even more preferably from 1000 to 3000 and most preferably from 1500 to 3000 Daltons.

For simplicity, the term enophile is used to include dienophile.

Enophiles have electron withdrawing moieties, such as ester, acid, cyanide and anhydride. Preferably the enophile is an electrophillic alkene or alkyne. Even more preferably is selected from the group consisting of maleic anhydride, fumaric acid, itaconic anhydride, acrylic acid and maleate esters and most preferably it is selected from the group consisting of maleic anhydride and fumaric acid.

By non-mineral oil is meant oil, comprising triglycerides, that has been obtained directly from plant or animal matter, including fish, rather than from a fossil feedstock.

Preferably, at least 80% by weight of the total triglycerides making up the oil contain one or more double bonds, more preferably 85 to 100%, still more preferably 90 to 100%, yet more preferably 95 to 100% and most preferably 100%. The amount of fully saturated triglycerides is preferably kept as low as possible as such triglycerides are unreactive to the enophile. The oily exudate seen on the surface of dried latex and paint films is thought to be this unreacted saturated material.

Being natural products, the composition of the oils varies significantly from year to year, the geographic location of the source and the degree of any further processing that may be carried out on the oil. Blending oils from different sources and even of different types not only produce a more consistent feedstock, but also enables oils having a triglyceride composition not found in nature to be produced.

However, even such blends are not ideal, because they consist of a complex mixture of triglycerides having saturated and mono and poly-unsaturated fatty acid portions. This inevitably results in a distribution of species being formed when the oils are subsequently reacted with polyfunctional material. There is also a risk of gelation.

Transesterification of oils, whereby the fatty acid portions between and within triglycerides are rearranged, can produce oils which, whilst not composed of the ideal triglyceride structure described above, nevertheless have more of the triglycerides with fewer unsaturated bonds, than the naturally occurring oil. Such oils are suitable for use in the present invention.

Optionally, the macromonomer is diluted with a suitable solvent, preferably one that is also a polymerisable monomer, in a final step. This ensures that the macromonomer does not solidify on cooling down from the reaction temperature making it easier to handle. Suitable such monomers which are also effective solvents include 2-ethyl hexyl acrylate, butyl acrylate and styrene.

Plant oils are preferred as their production consumes carbon dioxide rather than producing it.

Preferably the iodine value of the oil is less than 200, more preferably between 30 and 200 as the initial colour of the polymer film derived from it is less yellow. Even more preferably the iodine value is from 50 to 200, yet more preferably between 70 and 170, and most preferably from 100 to 160.

The proportion of the fatty acid component (of the triglycerides in the oil) having more than one double bond, is preferably less than 15%, more preferably from 0.5 to 15%, even more preferably from 1 to 12%, still more preferably from 1 to 10% and yet more preferably from 2 to 10% and most preferably from 5 to 10% by weight. It is such polyunsaturated fatty acids, especially having conjugated double bonds, which produce yellowing in dried paint films.

Suitable oils for use in the invention include, Palm oil, Soya bean oil, Cotton seed oil, Kapok oil, Mustard oil, Olive oil, Peanut oil, Rapeseed oil, Sesame oil and hydroxyl functional Castor oil. Preferably the oils for use in the invention are selected from the group consisting of Palm oil, Soya bean oil, Cotton seed oil, Kapok oil, Mustard oil, Olive oil, Peanut oil, Rapeseed oil, Sesame oil, Corn oil, Safflower oil, Sunflower oil and Tall oil. Even more preferably they are selected from the group consisting palm oil, sunflower oil, soya bean oil, safflower oil and rape seed oil.

They may be used alone or blended with others.

Palm oil, Safflower oil, Sunflower oil, Rape seed oil and Soya bean oil are especially useful oils in the invention as the macromonomers derived from them have good balance of reactivity and resistance to yellowing, when formulated into a binder, especially a polymer latex, for use in a coating composition.

All vegetable oils are a complex mixture of species. Nevertheless, average molecular weights are generally quoted in the region of 800 to 900 Daltons. Palm oil, for example has a molecular weight of 848 Daltons.

Preferably, the moiety on the ethylenically unsaturated monomer, reactive with the acid, ester or anhydride moiety of the enophile is a hydroxyl, amino or epoxide. Even more preferably, there is only one such moiety on the monomer.

Preferably the ethylenically unsaturated monomer reactive with the acid, ester or anhydride moiety of the enophile is selected from the group consisting or comprising hydroxyethyl (meth)acrylate, hydroxyl propyl (meth)acrylate, hydroxyl iso propyl methacrylate, hydroxyl butyl (meth)acrylate, allyl alcohol, glycerol methacrylate, glycidyl (meth)acrylate, allyl amine, tert-butyl aminoethyl methacrylate. More preferred are hydroxy ethyl acrylate and hydroxyl ethyl methacrylate and most preferred is hydroxyl ethyl methacrylate.

The reaction of the ethylencially unsaturated monomer with the adduct is preferably carried out in the presence of a polymerisation inhibitor in order to prevent the monomer from homopolymerising. A suitable such inhibitor is phenothiazine.

Preferably the chain extender material comprises hydroxyl, amine, oxirane or isocyanate moieties. More preferably, it comprises at least two moieties capable of reacting with the acid, ester or anhydride moiety of the enophile. Nevertheless, it is possible that a trifunctional material is acceptable if one of the moieties is much slower to react than the other two. For example, this is thought to be the case when glycerol is used, where the secondary hydroxyl group is less reactive than the two primary hydroxyl groups. Preferably, the chain extender material is glycerol as it is readily obtained from sustainable plant material.

The mole ratio of oil:enophile is preferably less than or equal to 1, more preferably from 0.3 to 1.0, even more preferably from 0.50 to 1.00, still more preferably from 0.55 to 0.75 and most preferably from 0.60 to 0.70. The resulting excess of enophile helps to reduce the amount of unreacted oil thereby limiting the tendency to produce exudate.

The mole ratio of oil:chain extender is preferably greater than 1.8, more preferably from 1.8 to 10.0, even more preferably from 2.0 to 7.5, still more preferably from 2.5 to 5 and most preferably from 3.0 to 3.5.

The mole ratio of unsaturated monomer:oil is preferably less than 1:1, more preferably it is between 0.25:1 and 1:1, even more preferably from 0.3:1 to 0.9:1, yet more preferably from 0.5:1 and 0.85:1 and most preferably from 0.6:1 to 0.85:1. At these ratios, polymer films derived from such macromonomers tend to be harder than films derived from macromonomers of higher unsaturated monomer content. Furthermore, the lower level of unsaturated monomer relative to the oil results in an increased content of renewable resource in the macromonomer and, thus, the final coating, which is environmentally beneficial. Finally, due to the high energy content required to produce the ethylenically unsaturated monomer, a significant cost saving is also realised.

The mole ratio of oil:enophile:unsaturated monomer:chain extender is preferably 1.00:1.50:0.75:0.30. Even more preferably the oil is Soya bean oil, the enophile is maleic anhydride, the unsaturated monomer is hydroxyl ethyl (meth)acrylate—most preferably hydroxyl ethyl methacrylate, and the chain extender is glycerol.

The reaction of the oil with the enophile is thought to produce an adduct of the triglycerides comprising the oil, and the enophile. The adduct having an acid, ester or anhydride moiety reacts with a suitable functional moiety on the ethylenically unsaturated monomer to form an intermediate polymerisable triglyceride monomer. Further reaction with a chain extender material, increases the molecular weight of the intermediate thereby ensuring that the proportion of triglyceride not functionalised with the unsaturated monomer ii) is kept to a minimum. This reduces the tendency for exudation form polymers comprising such monomers.

As the macromonomer is the product of an oil comprising a mixture of triglycerides, some of which have a functionality greater than one, with other reactants also having functionality greater than one, the macromonomer is thought to be a complex mixture of species.

In practice, the reaction of the triglycerides with the enophile to form the adduct is further complicated because the triglycerides (of the oil) themselves can have differing degrees of unsaturation (ie mono-, di- or tri-ene).

The degree of conjugation of any unsaturation greater than one; that is di- and tri-enes, also affects the reaction mechanism by which the adduct is produced. For enes and unconjugated dienes, the preferred reaction is thought to be the Alder-ene reaction and for conjugated dienes, the preferred reaction is the Diels-Alder reaction.

Figure 2:
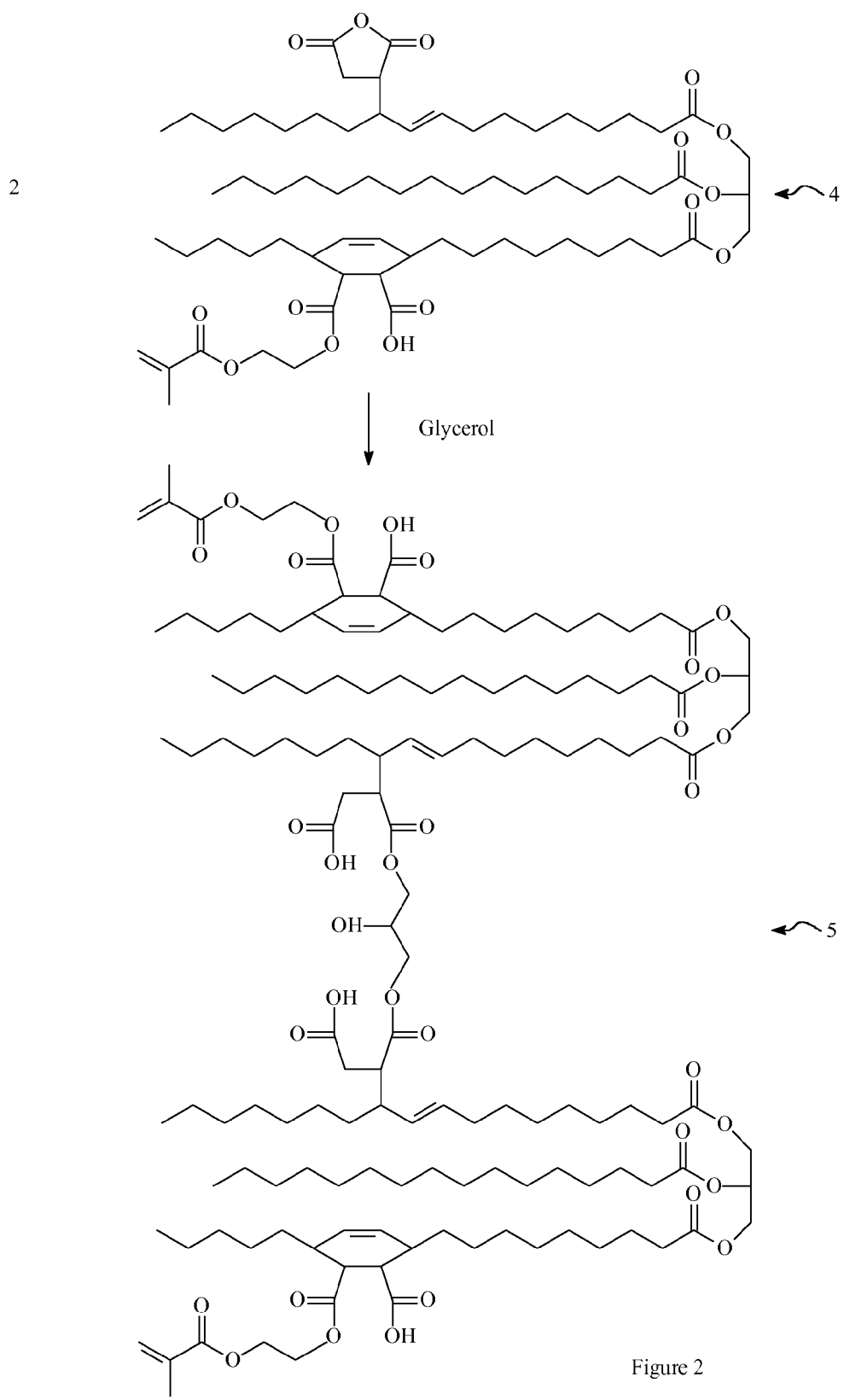

FIGS. 1 and 2 show a simplified and idealised diagrammatic scheme for the formation of one of the species that make up the macromonomer of the invention. In this case the enophile is maleic anhydride; the unsaturated monomer is hydroxyl ethyl methacrylate and the chain extender is glycerol.

FIG. 1 shows a reaction scheme of a triglyceride (1) reacting with maleic anhydride and hydroxyl ethyl methacrylate. The triglyceride comprises a saturated fatty acid, a mono-unsaturated fatty acid and an unconjugated diene fatty acid. In the presence of sufficient iodine, any unconjugated diene becomes conjugated as shown in structure (2). This triglyceride comprising a conjugated diene fatty acid reacts with the maleic anhydride via the Diels-Alder reaction to form the adduct containing the cyclic hexene structure depicted in (3). Furthermore, in some circumstances any non-conjugated unsaturated double bond will react with the maleic anhydride via the Alder-ene reaction. For simplicity, we show both the mono-unsaturated and the diene reacted with the maleic anhydride on the same triglyceride molecule. The extent to which this happens, if at all, will depend on the relative molar amounts of the enophile,and triglycerides of the oil; and the level of unsaturation and conjugation.

It is thought that the adduct (3) reacts with the hydroxyl ethyl methacrylate to form a structure depicted as (4).

FIG. 2 shows the reaction of structure 4 with glycerol to form one of the species (5) of the macromonomer.

Of course, because of the numerous multi-functional species formed during the reaction, the measured molecular weight of the macromonomer is much higher than as depicted in the drawings and rather is as hereinbefore described.

The oil is represented by an idealised triglyceride structure (1) comprising palmitic acid, oleic acid and linoleic acid.

In a further aspect of the invention there is provided a process of making the macromonomer comprising the steps of i) reacting an unsaturated non-mineral oil with an enophile having an acid, ester or anhydride moiety to form an adduct ii) reacting the adduct with an ethylencially unsaturated monomer having a moiety reactive with the acid, ester or anhydride moiety of the enophile to form an intermediate iii) reacting the intermediate of step ii) with a chain extender having at least two moieties reactive with the acid, ester or anhydride moiety of the enophile to form the ethylenically unsaturated macromonomer.

The intermediate is of lower molecular weight than the macromonomer.

Preferably the molecular weight of the macromonomer formed in step iii) is as previously defined.

The reaction of step i) is preferably carried out above 150° C., more preferably above 180° C., even more preferably from 200 to 300° C. and most preferably from 200 to 250° C.

Where the fatty acid component of the triglycerides comprising the oil contains less than 30% of fatty acids having conjugated double bonds, it is preferred to heat the oil in the presence of iodine at a temperature of from 80 to 250° C., more preferably from 80 to 200° C., even more preferably from 90 to 110° C. and most preferably 100° C. The presence of the iodine serves to convert the unconjugated double bonds, for example of linoleic acid, to conjugated double bonds which are thus able to react with the enophile and/or dienophile, for example maleic anhydride, via the preferred Diels Alder reaction. Preferably the ratio of iodine:oil is from 0.002:1 to 0.010:1 calculated on a molar basis. On a weight basis this is equivalent to about 0.0006:1 to 0.003:1 depending on the molecular weight of the oil. We have found that macromonomer produced including this step produces less yellowing in a polymer binder comprising the macromonomer than binder derived from macromonomer produced without the iodine step. This is even more evident when such binders are used to make pastel or white paint.

The reaction of the ethylenically unsaturated monomer with the adduct in step ii) of the process is preferably carried out in the presence of a polymerisation inhibitor in order to prevent the monomer from homopolymerising. A suitable such inhibitor is phenothiazine.

Depending on the choice of unsaturated oil, the resultant neat macromonomer can vary in appearance at room temperature from a reasonably fluid liquid to a greasy or even waxy consistency. The oils of low iodine value, say less than 100, tend to be soft solid since they are more saturated than the higher iodine value oils.

In a further aspect of the invention, there is provided an addition polymer comprising the macromonomer as hereinbefore described. Preferably the polymer is polymerised with other ethylenically unsaturated monomers. Examples of suitable ethylenically unsaturated monomers include (meth) acrylic acid esters, amides, and nitriles, vinyl monomers and vinyl esters.

It is preferred that the polymer comprises more than 6 wt % of the macromonomer of the invention, more preferably from 6 to 80 wt %, even more preferably from 15 to 75 wt % and most preferably from 20 to 60 wt %.

Using the nomenclature of (meth)acrylate to represent both acrylate and methacrylate, examples of suitable other acrylic acid esters and methacrylic acid esters are alkyl esters, preferably methyl (meth)acrylate, ethyl (meth)acrylate, propyl (meth)acrylate, butyl (meth)acrylate, 2-ethyl hexyl (meth) acrylate and alkoxy poly(oxyethylene) (meth)acrylate. Small amounts of methacrylic acid and/or acrylic acid may also be used. Hydroxy functional monomers such as hydroxy ethyl (meth)acrylate and hydroxy isopropyl (meth)acrylate may be included also. Examples of suitable vinyl monomers include styrene and alpha methyl styrene, vinyl propionate, vinyl butyrate, vinyl acetate and vinyl versatate. Preferably the addition polymer is derived from the esters of acrylic acid, methacrylic acid and optionally styrene and/or its derivatives. More preferably, the other monomers are styrene and 2-ethyl hexyl acrylate.

The glass transition temperature, or Tg, of the polymer comprising the macromonomer of the invention may be varied by copolymerising monomers of appropriate Tg. In this way copolymers which are hard, soft or of intermediate Tg can be made, which can produce a wide range of physical film properties such as tack (or stickiness), hardness and extensibility.

Preferably the Tg of the polymer is from −70 to 185° C., more preferably from −20 to 120° C. More preferably the polymer is suitable for use as a binder in coatings especially in architectural coating compositions. For such binder polymer dispersions the preferred range is from −20 to 120° C., yet more preferably from −15 to 60° C., even more preferably from −10 to 25° C. and most preferably from −10 to 10° C. as this produces a more durable paint which is better resistant to knocks and scuffs.

More preferably, the polymer is in the form of an aqueous composition and still more preferably is an aqueous dispersion of polymer microparticles. By aqueous is meant that at least 50% by weight of the carrier liquid is water, more preferably more than 75% and most preferably the carrier liquid is water.

Preferably the polymer microparticles have a mean diameter of from 0.05 to 2 microns, more preferably from 0.05 to 1.0 microns, still more preferably from 0.05 to 1.0 microns and most preferably from 0.05 to 0.3 microns.

Optionally, the microparticles are of the core-shell type having a core polymer composition different from the shell polymer composition. Preferably, the core:shell ratio calculated on a weight basis is from 1:8 to 2:1, more preferably from 1:2.

The ethylenically unsaturated monomers are caused to copolymerise by heating the monomer, in a carrier liquid-preferably water, containing polymerisation initiators, preferably to a temperature of from 30° C. to 150° C., preferably from 40° C. to 80° C. More preferably the polymerisation process used is an aqueous emulsion polymerisation process. In such a case the maximum polymerisation temperature should not exceed 98° C. Even more preferably, where redox initiator combinations are used, the preferred polymerisation temperature is from 20° C. to 80° C. and most preferably from 30° C. to 70° C.

Suitable emulsion polymerisation initiators include oxidants, for example, peroxides such as tertiary butyl hydroperoxide, hydrogen peroxide and cumene hydroperoxide; persulphates such as potassium persulphate and ammonium persulphate; azo types such as 4,4' azobis (4-cyanopentanoic acid). Preferably from 0.002% by weight to 5% by weight of the initiator is used, calculated on the amount of ethylenically unsaturated monomers, more preferably from 0.05 to 2% and most preferably from 0.1 to 1%.

Reductants may be used in combination with the oxidant to form so called redox couples. This enables the polymerisation to be run at lower temperature than when relying on thermal decomposition alone. Suitable examples of such oxidants include sodium ascorbate, sodium metabisulphite and sodium formaldehyde sulphoxylate. Suitable examples of redox couples include tertiary butyl hydroperoxide with ascorbic acid or sodium ascorbate, sodium metabisulphite or sodium formaldehyde sulphoxylate; hydrogen peroxide with ascorbic acid, sodium ascorbate, sodium metabisulphite or sodium formaldehyde sulphoxylate; cumene hydroperoxide with ascorbic acid, sodium ascorbate or sodium metabisulphite or sodium formaldehyde sulphoxylate. More preferred is the redox couple tertiary butyl hydroperoxide with sodium ascorbate.

Optionally, metal salts such as copper, chromium and iron salts can be added when redox pairs are used. Such metals, usually in the form of water soluble salts, for example iron(II) sulphate, are especially useful where the natural level of dissolved metals in the reaction mixture are low. This can occur when a glass-lined reactor is used or a metal chelating agent is present. The presence of the added metal salts ensures that the redox system works effectively. Preferably the level of added metal salt is kept to a minimum to avoid discolouration of the dispersion itself and any coatings derived from it. This is generally less of a problem for adhesives.

The preferred initiator system is the redox combination of tertiary butyl hydroperoxide and ascorbic acid, the latter optionally in the form of sodium ascorbate. Such redox combinations allow the polymerisation to be carried out or around ambient temperature such as from 30 to 55° C.

In a further aspect of the invention there is provided a process of producing an aqueous dispersion of polymer microparticles derived from a monomer mixture comprising the macromonomer and other ethylenically unsaturated monomers, as hereinbefore described.

Preferably the process comprises the steps of
i) making an emulsion of ethylenically unsaturated monomers comprising the macromonomer and other monomers, in aqueous medium, preferably water, containing surfactant
ii) charging from 5 to 25% by weight of the monomer emulsion to a polymerisation vessel and causing it to polymerise to form polymer microparticles of mean particle diameter of from 0.05 to 3 microns
iii) feeding the remaining monomer emulsion of step i) to the vessel in the presence of the microparticles of step ii) and causing it to polymerise and grow them to form the final microparticles of mean particle diameter of from 0.05 to 2.0 microns.

More preferably, the process comprises the steps of
i) making an aqueous emulsion comprising the macromonomer and no other monomer
ii) charging the emulsion to a polymerisation vessel and adding at least some of a mixture of neat comonomers to the vessel and causing the combination of comonomers and macromonomer to polymerise to form polymer microparticles of mean particle diameter of from 0.05 to 2 microns
iii) feeding a neat mixture of the remaining comonomers to the vessel in the presence of the microparticles of step ii) and causing it to polymerise and grow them to form the final microparticles.

This has the advantage that there is no need to make an aqueous emulsion of the macromonomer and the other ethylenically unsaturated monomers thereby saving time.

Furthermore, it ensures that the macromonomer of the invention is polymerised into the particles.

In a yet further aspect of the invention there is provided a coating composition comprising the addition polymer as hereinbefore described. Preferably, the coating is aqueous. More preferably the coating is an architectural paint for use on the interior and exterior surfaces of structures such as found in homes, offices and gardens. Even more preferably, the paint is of non-Newtonian rheology, even more preferably, thixotropic rheology.

The coating composition may also contain ingredients selected from the group consisting pigments, fillers, waxes, extenders, rheological modifiers, dispersants, anti-foams, plasticisers, crosslinking agents, flow aids and biocides.

Materials Used in the Examples

RD Palm Oil is available from Hampshire Commodities, Fleet, Hampshire, UK, GU51 3SR.

Sunflower oil is available from Kerfoot, The Olive House, Standard Way Industrial Estate, North Allerton, North Yorkshire England.

tert-butyl hydroperoxide (t-BHP) is available from Akzo-Nobel

Disponil A4066 is available from Cognis (UK) Ltd.

Tests

Molecular Weight was determined by Gel Permeation Chromatography (GPC) using a Waters 150CV fitted with a refractive index detector. The columns used were 2×30 cm PLGel Mix D GPC columns at a temperature of 35° C. Polystyrene (ex. Polymer Laboratories) was used as the standard. The test material was dissolved in tetrahydrofuran at a concentration of 1 mg cm$^{-3}$. The flow rate was 1 cm$^3$ min$^{-1}$.

Examples of the invention will now be described.

MACROMONOMER EXAMPLE 1

| MM 1 | | |
| --- | --- | --- |
| | g | wt % |
| RD Palm oil | 1698.59 | 56.620 |
| Maleic anhydride | 294.30 | 9.820 |
| Iodine | 2.55 | 0.085 |
| Phenothiazine | 3.38 | 0.113 |
| Hydroxy ethyl methacrylate | 195.51 | 6.517 |
| Glycerol | 55.33 | 1.845 |
| 2-ethyl hexyl acrylate | 250.00 | 25.000 |

To a 5 liter round bottomed flask fitted with a water cooled condenser, means to provide a nitrogen blanket and an anchor stirrer operating at 75 rpm was added the RD Palm oil and maleic anhydride whilst stirring. The mixture was heated to 100° C. and the iodine was added; the temperature was held for 30 minutes. The temperature was raised to 200° C. and held there for 30 minutes and then increased to 220° C. After 5 hours and thirty minutes it was cooled to 200° C. and the phenothiazine was added (which helps to prevent the homopolymerisation of hydroxyl ethyl methacrylate). After five minutes the hydroxy ethyl methacrylate was added over a period of 15 minutes and held at 200° C. for an hour, following which the glycerol was added. After an hour at 200° C. the batch was cooled to 80° C. and the 2-ethyl hexyl acrylate was added and then filtered through lambswool.

The resulting macromonomer dissolved in 2-ethyl hexyl acrylate is a clear, low viscosity liquid that is easy to handle.

LATEX EXAMPLE

Latex 1

A latex was made using the macromonomer MM 1 and the following ingredients using the following procedure

| | g | wt % |
| --- | --- | --- |
| Initiator | | |
| t-BHP/1 | 5.48 | 0.498 |
| Monomer Pre-emulsion | | |
| MM 1 | 171.73 | 15.612 |
| Styrene | 260.35 | 23.668 |
| 2-ethyl hexyl acrylate | 83.12 | 7.556 |
| Ammonia (25% solution) | 8.02 | 0.729 |
| Demin water/1 | 444.42 | 40.402 |
| Disponil A4066 | 43.24 | 3.931 |
| Reductant Solution | | |
| Demin water/2 | 77.80 | 7.073 |
| Sodium ascorbate | 3.10 | 0.282 |
| t-BHP/2 | 2.74 | 0.249 |

Prepare 523.22 g of Monomer Pre-emulsion by mixing the indicated weights of macromonomer MM 1, styrene, 2-EHA and adding the ammonia under gentle stirring for about 10 minutes, adding the ammonia dropwise. Add this monomer mixture to a solution of 444.42 g of Demin/1 and 43.24 g Disponil A4066 under high shear mixing conditions using a Silverson homogeniser to form an emulsion of monomer in water until the mean droplet size is about 150 nm and there are no monomer droplets greater than 2000 nm. This will require about 20 minutes.

Prepare the reductant solution by dissolving the sodium ascorbate in water

To a 2 l parallel sided vessel fitted with a propeller stirrer, condenser and a nitrogen blanket, add 350.00 g of the Monomer Pre-emulsion and raise the temperature to 50° C. and add t-BHP/1. After 5 minutes at this temperature add 20.23 g of the reductant solution. Allow the batch to exotherm for 5 minutes and then feed the remainder of the Monomer Pre-emulsion linearly over 60 minutes whilst concurrently feeding 26.97 g of the Reductant solution, linearly. Maintain at 50° C. for a further 15 minutes and then add 6.74 g of the Reductant solution and hold for a further 15 minutes. Add t-BHP/2 and maintain temperature for a further 5 minutes after which time add the remaining Reductant solution, 26.97 g linearly over 30 minutes. Maintain at 50° C. for 15 minutes and then cool and filter through 80 mesh nylon.

There was very little build-up on the reactor walls or the stirrer and the latex was bit free.

The latex constants were pH: 7.2 subsequently adjusted to 8.5 weight solids: 50.0%

Mean particle size was 145 nm measured using a Malvern Mastersizer

PAINT EXAMPLE

Paint 1

A semi-gloss paint was made using Latex 1 and the ingredients listed below.

| | wt % |
|---|---|
| Load the following ingredients to a dispersion vessel Millbase stage | |
| Tap water | 6.673 |
| Benzyl alcohol | 1.200 |
| Tamol 731 | 1.850 |
| Dispelair CF 823 | 0.173 |
| Start disperser on low speed and begin adding pigmentation. Increase speed as millbase thickens to maintain a good vortex. | |
| China clay supreme | 6.130 |
| Tioxide TR92 | 18.240 |
| Run 20 minutes. Check dispersion is less than 20μ. Then add the other materials adjusting speed as required. | |
| Dispelair CF823 | 0.173 |
| Product V189 | 0.020 |
| Tap water | 3.000 |
| Aquaflow NHS 300 | 0.750 |
| Acrysol SCT-275 | 0.750 |
| SUB-TOTAL | 38.959 |

Run 10 minutes
Cover and allow millbase to cool before making into finished product.

Paint Stage

| Load millbase to a clean vessel | |
|---|---|
| Millbase | 38.959 |
| Add with stirring | |
| Latex 1 | 44.152 |
| Tap water | 10.000 |
| Pre blend | |
| Tap water | 2.850 |
| Acrysol TT935 | 0.150 |
| Run 10 minutes Adjust to viscosity with | |
| Tap water | 3.889 |
| TOTAL | 100.000 |

Paint Evaluation

The following tests were carried out on Paint 1

Viscosity 9-10 poise measured at 25° C. using a Rotothinner operating at 562 rpm.

Gloss

The paint was drawn down on a glass panel, allowed to dry and the gloss measured at 60 and 85°

Gloss 60°: 48%

Gloss 85°: 88%

Hardness

Erichsen Hardness after 7 days at ambient temperature: 38 seconds.

Fingernail hardness: acceptable

White index: 77.5

Water Resistance

Wet scrub resistance: 4.87 mg/cm$^2$ after 2000 cycles

Water Spot 2 ml of tap water was dropped onto a 25 micron dried coat of the paint and covered with a watch glass and left to stand for 2 hours and assessed the paint assessed. No damage or permanent loss of gloss noted.

MACROMONOMER EXAMPLE 2

MM 2

A second macromonomer was made according to the invention.

For convenience, 2 kg of stock solution of maleinised soya bean oil was made using the ingredients and method describe below.

To a 3 liter round bottomed flask fitted with a water cooled condenser, means to provide a nitrogen blanket and an anchor stirrer operating at 75 rpm was added 1707.814 g soybean oil and 286.107 g maleic anhydride. The mixture was heated to 100° C. and 2.488 g iodine was added. The temperature was raised to 200° C. and held there for 30 minutes and then increased to 220° C. After 4 hours it was cooled to room temperature and filtered through lambswool.

This was converted to the macromonomer MM 2 as follows:

| | g | wt % |
|---|---|---|
| Maleinised Soya bean oil | 359.32 | 89.697 |
| Phenothiazine | 1.20 | 0.300 |
| Hydroxy ethyl acrylate | 30.42 | 7.594 |
| Glycerol | 9.65 | 2.409 |

To a 700 ml round bottomed flask fitted with a water cooled condenser, means to provide a nitrogen blanket and an anchor stirrer operating at 75 rpm was added 359.32 g of the maleinised soya bean oil described above. The mixture was heated to 100° C. and 1.20 g phenothiazine was added. The mixture was then heated to 200° C. and the 30.42 g Hydroxyethylacrylate was fed in via a dropping funnel over 15 minutes. The mixture was held for 50 minutes at 200° C. then cooled to 180° C. 9.65 g of glycerol was added as a shot and the mixture held for 30 minutes to give the final macromonomer which was then cooled back to approximately 70° C. and filtered through lambswool.

LATEX EXAMPLE 2

Latex 2

The macromonomer MM 2 was converted to a latex using the following ingredients and method.

|  | g | wt % |
|---|---|---|
| Initiator shot 1 | | |
| Tertiary butyl hydroperoxide/1 | 4.93 | 0.448 |
| Monomer Pre-emulsion | | |
| MM 2 | 115.92 | 10.544 |
| Styrene | 225.13 | 20.479 |
| 2-ethyl hexyl acrylate | 122.62 | 11.150 |
| Ammonia (25% solution) | 7.22 | 0.657 |
| Surfactant solution | | |
| Demin water/1 | 509.98 | 46.390 |
| Disponil A4066 | 38.92 | 3.538 |
| Reductant Solution 1 | | |
| Demin water/2 | 46.68 | 4.247 |
| Sodium ascorbate/1 | 1.86 | 0.169 |
| Ferrous Sulphate Heptahydrate | 0.01 | 0.001 |
| Initiator Shot 2 | | |
| Tertiary butyl hydroperoxide/2 | 2.46 | 0.246 |
| Reductant Solution 2 | | |
| Demin water/3 | 23.34 | 2.123 |
| Sodium ascorbate/2 | 0.09 | 0.008 |

Prepare 1019.78 g of Monomer Pre-emulsion by mixing the indicated weights of macromonomer MM 2, styrene, 2-ethyl hexyl acrylate and adding the ammonia under gentle stirring for about 10 minutes, adding the ammonia dropwise. Add this monomer mixture to the surfactant solution of 509.98 g of Demin/1 and 38.92 g Disponil A4066 under high shear mixing conditions using a Silverson homogeniser to form an emulsion of monomer in water until the mean droplet size is about 150 nm and there are no monomer droplets greater than 2000 nm. This will require about 20 minutes.

Prepare the reductant solutions by dissolving the sodium ascorbate and ferrous sulphate heptahydrate if required in water To a 1 l parallel sided vessel fitted with a propeller stirrer, condenser and a nitrogen blanket, add 100% of the Monomer Pre-emulsion and raise the temperature to 50° C. and add the initiator shot. After 5 minutes at this temperature add 37.5% of reductant solution 1. Hold for 15 minutes and then feed in 62.5% of Reductant solution 1 over 60 minutes. Hold at 50° C. for a further 5 minutes and then add initiator shot 2 and hold for 5 minutes. Add reductant solution 2 linearly over 15 minutes. Maintain at 50° C. for 5 minutes and then cool and filter through 80 mesh nylon.

There was very little build-up on the reactor walls or the stirrer and the latex was bit free.

The latex constants were
Weight solids: 45.0%
Mean particle size 124nm.
Paint 2

Latex 2 was converted to a paint according to the method used for Paint 1 but using the following ingredients
Millbase

| Description | g |
|---|---|
| Water (Mains) | 20.080 |
| Texanol | 3.012 |
| Orotan/Tamol 731 A | 5.020 |
| Disponil A1580 | 2.510 |
| Dispelair CF823 | 0.434 |
| China Clay Supreme | 15.060 |
| Microdol H600 | 15.060 |
| Tioxide TR92 | 45.782 |
| Dispelair CF823 | 0.434 |
| Rocima V189 | 0.050 |
| Water (Mains) | 3.499 |
| Aquaflow NHS 300 | 1.255 |
| Acrysol SCT-275 | 1.255 |
| | 113.450 |

Paint

|  | g |
|---|---|
| Millbase | 113.45 |
| Latex 2 | 133.05 |
| Ammonia (26%) | 0.02 |
| Water | 3.48 | pH 7.3
Rotothinner viscosity at 25° C. 0.74 Pa·s
Initial whiteness 77.1

MACROMONOMER EXAMPLE 3

MM 3

|  | g | % |
|---|---|---|
| Sunflower oil | 450.00 | 76.77 |
| Maleic anhydride | 73.50 | 12.54 |
| Phenothiazine | 0.75 | 0.13 |
| Hydroxy ethyl methacrylate | 52.56 | 8.97 |
| Ethylene glycol | 9.30 | 1.59 |

450 g (0.5 Moles) of Sunflower Oil was charged to a 1 liter round bottomed flask fitted with a mechanical stirrer, nitrogen inlet and a condenser. The oil was sparged with nitrogen to eliminate oxygen from the system. 73.50 g maleic anhydride (0.75 Moles) was added to the reactor and the reaction temperature was raised to 200° C. It was held at this temperature for 60 mins after which it was increased to 220° C. and held for at least 4 hours. The reaction was then cooled to 200° C. and 0.75 g of phenothiazine (0.15% based upon oil charge) was added and allowed to disperse for 5 minutes. 52.56 g of hydroxyl ethyl methacrylate (0.75 Moles) was then added to the reaction from a dropping funnel over a period of 30 minutes. Following the addition the reaction was then held for a further 60 minutes at 200° C. Ethylene Glycol was then added, 9.3 g (0.3 Moles) and the reaction was held at 200° C. for a further 60 minutes during which time the macromonomer, MM 3, formed. The reaction was then allowed to cool to below 100° C. and the macromonomer was stored until required.

The macromonomer MM 3 was characterised to determine the molecular weight.

Mw 9060 Daltons
Mn 2200 Daltons.

LATEX EXAMPLE 3

Latex 3

The macromonomer MM 3 was converted to a latex using the following ingredients and method.

| | g |
|---|---|
| Initiator shot 1 | |
| Tertiary butyl hydroperoxide/1 | 5.48 |
| Monomer Premix | |
| MM 3 | 128.80 |
| Styrene | 260.35 |
| 2-ethyl hexyl acrylate | 126.05 |
| Ammonia (25% solution) | 8.02 |
| Surfactant solution | |
| Demin water/1 | 444.42 |
| Disponil A4066 | 32.63 |
| Reductant Solution 1 | |
| Demin water/2 | 51.87 |
| Sodium ascorbate/1 | 2.07 |
| Initiator Shot 2 | |
| Tertiary butyl hydroperoxide/2 | 2.74 |
| Reductant Solution 2 | |
| Demin water/3 | 25.93 |
| Sodium ascorbate/2 | 1.04 |

Prepare 874.06 g of Monomer Pre-emulsion by mixing the indicated weights of macromonomer MM 1, styrene, 2-EHA and adding the ammonia under gentle stirring for about 10 minutes, adding the ammonia dropwise. Add this monomer mixture to the surfactant solution solution of 444.42 g of Demin/1 and 43.25 g Disponil A4066 under high shear mixing conditions using a Silverson homogeniser to form an emulsion of monomer in water until the mean droplet size is about 150 nm and there are no monomer droplets greater than 2000 nm. This will require about 20 minutes.

Prepare the reductant solutions by dissolving the sodium ascorbate in water.

To a 1 l parallel sided vessel fitted with a propeller stirrer, condenser and a nitrogen blanket, add the Monomer Pre-emulsion and raise the temperature to 50° C. and add the initiator shot. After 5 minutes at this temperature add 15% of reductant solution 1. Hold for 5 minutes and then feed 60% of Reductant solution 1. Hold at 50° C. for a further 15 minutes and then add 25% of reductant solution 1 and hold for 15 minutes. Add initiator shot 2 and hold for 5 minutes. Add reductant solution 2 linearly over 30 minutes. Maintain at 50° C. for 15 minutes and then cool and filter through 80 mesh nylon.

There was very little build-up on the reactor walls or the stirrer and the latex was bit free.

COMPARATIVE EXAMPLE A

A macromonomer, labelled MM-A, was prepared without using any chain extender material.

Macromonomer MM-A

Maleinised Palm oil

For convenience 2.7 l of a stock solution of the maleinised Palm Oil was made using the following ingredients and according to the method described below.

To a 5 liter round bottomed flask fitted with a water cooled condenser, means to provide a nitrogen blanket and an anchor stirrer operating at 75 rpm was added 2253.32 g RD Palm oil and 442.84 g maleic anhydride. The mixture was heated to 100° C. and 3.84 g iodine was added. The temperature was raised to 200° C. and held there for 30 minutes and then increased to 220° C. After 5 hours and thirty minutes it was cooled to room temperature and filtered through lambswool.

This was converted to the macromonomer MM-A as follows:

| | g | wt % |
|---|---|---|
| Maleinised Palm oil | 189.999 | 85.836 |
| Phenothiazine | 0.332 | 0.150 |
| Hydroxy ethyl methacrylate | 31.021 | 14.014 |

To a 700 ml round bottomed flask fitted with a water cooled condenser, means to provide a nitrogen blanket and an anchor stirrer operating at 75 rpm was added 189.999 g of the maleinised Palm oil described above. The mixture was heated to 100° C. and 0.332 g phenothiazine was added. The mixture was then heated to 200° C. and the 31.021 g Hydroxyethylmethacrylate was fed in via a dropping funnel over 15 minutes. The mixture was held for 1 hour at 200° C. to give the final macromonomer which was then cooled back to approximately 70° C. and filtered through lambswool.

Latex A

The macromonomer MM-A was converted to a latex using the following ingredients and method.

| | g | wt % |
|---|---|---|
| Prefeed reductant shot | | |
| Sodium Ascorbate/1 | 0.710 | 0.118 |
| Demin Water/1 | 6.358 | 1.060 |
| Monomer Pre-emulsion | | |
| MM-A | 69.905 | 11.651 |
| Styrene | 141.304 | 23.551 |
| 2-ethyl hexyl acrylate | 68.412 | 11.402 |
| Ammonia (25% solution) | 4.354 | 0.726 |
| Surfactant solution | | |
| Demin water/2 | 265.221 | 44.203 |
| Disponil A4066 | 23.472 | 3.912 |
| Initiator Solution | | |
| Tertiary butyl hydroperoxide | 2.972 | 0.495 |
| Demin Water/3 | 5.419 | 0.903 |
| Reductant Solution 1 | | |
| Demin water/4 | 5.419 | 0.903 |
| Sodium ascorbate/2 | 0.473 | 0.079 |
| Reductant Solution 2 | | |
| Demin water/5 | 5.419 | 0.903 |
| Sodium ascorbate/3 | 0.562 | 0.094 |

Prepare 572.668 g of Monomer Pre-emulsion by mixing the indicated weights of macromonomer MM-A, styrene, 2-EHA and adding the ammonia under gentle stirring for about 10 minutes, adding the ammonia dropwise. Add this monomer mixture to the surfactant solution solution of 265.221 g of Demin/1 and 23.472 g Disponil A4066 under high shear mixing conditions using a Silverson homogeniser to form an emulsion of monomer in water until the mean droplet size is about 150 nm and there are no monomer droplets greater than 2000 nm. This will require about 20 minutes.

Prepare the pre-feed reductant shot by dissolving the sodium ascorbate in water.

Prepare the reductant solutions by dissolving the sodium ascorbate in water

Prepare the initiatior solution by dissolving tertiary butyl hydroperoxide in water.

To a 1 l parallel sided vessel fitted with a propeller stirrer, condenser and a nitrogen blanket, add 29.3% of the Monomer Pre-emulsion and raise the temperature to 30° C. and add prefeed reductant shot. After 5 minutes at this temperature add 0.420 g of the initiator solution. Hold for 15 minutes and then feed the remainder of the Monomer Pre-emulsion linearly over 75 minutes whilst concurrently feeding Reductant solution 1 over 95 minutes and 7.132 g of initiator solution over 95 minutes. 20 minutes into the preemulsion feed raise the temperature to 40° C. and 60 minutes into the preemulsion feed raise the temperature to 50° C. Hold at 50° C. for a further 15 minutes and then add 0.839 g the initiator solution and hold for 10 minutes. Add reductant solution 2 linearly over 30 minutes. Maintain at 50° C. for 15 minutes and then cool and filter through 80 mesh nylon.

There was very little build-up on the reactor walls or the stirrer and the latex was bit free.

The latex constants were
pH: 6.9
weight solids: 49.5%
Rotothinner viscosity at 25° C. 0.19 Pa·s
MFFT was 15° C.
Comparative Paint A The millbase and method as described in Paint 2 was used and the Latex A was converted to a paint using the ingredients listed below.

| Paint | |
|---|---|
| | g |
| Millbase | 113.45 |
| Latex A | 119.75 |
| Ammonia (26%) | 0.02 |
| Water | 16.78 | pH 7.1
Rotothinner viscosity at 25° C. 0.77 Pa·s
Initial whiteness 76.0
Evidence of oily exudate
Standard Paint Comparative Paint B is based on a conventional vinyl acetate/butyl acrylate copolymer and does not contain any monomer made from a renewable resource. It is an aqueous binder commonly used in paint compositions and the paint properties are acceptable.

The millbase and method as described in Paint 2 was used and the Latex A was converted to a paint using the ingredients listed below.

| Paint | |
|---|---|
| | g |
| Millbase | 113.45 |
| VA/BA latex | 116.25 |
| Ammonia (26%) | 0.02 |
| Water | 20.28 | pH 7.3
Rotothinner viscosity at 25° C. 0.26 Pa·s
Initial whiteness 81.4

Paint examples 1 and 2 have good white index values and are commercially acceptable. Comparative Paint A has slight lower white index and thus is more yellow with some exudate.

The invention claimed is:

1. A polymerisable ethylenically unsaturated macromonomer being the reaction product of
   i) an adduct formed from the reaction of an unsaturated non-mineral oil reacted with an enophile having an acid, ester or anhydride moiety and
   ii) an ethylenically unsaturated monomer having a moiety reactive with the acid, ester or anhydride moiety of the enophile and
   iii) a chain extender material having at least two moieties reactive with the acid, ester or anhydride moiety of the enophile.

2. The ethylenically unsaturated macromonomer according to claim 1 wherein the unsaturated non-mineral oil has an iodine value between 30 and 200.

3. The ethylenically unsaturated macromonomer according to claim 1 wherein the unsaturated non-mineral oil is obtained from plant matter.

4. The ethylenically unsaturated macromonomer according to claim 1 wherein the unsaturated non-mineral oil is selected from the group consisting of palm oil, sunflower oil, soya bean oil, safflower oil and rape seed oil.

5. The ethylenically unsaturated macromonomer according to claim 1 wherein the enophile is selected from the group consisting of maleic anhydride, itaconic anhydride, fumaric acid, acrylic acid and maleate esters.

6. The ethylenically unsaturated macromonomer according to claim 1 wherein the monomer reactive with the acid, ester or anhydride of the enophile is selected from the group consisting of hydroxyl ethyl (meth)acrylate, hydroxyl propyl (meth)acrylate, hydroxyl iso propyl methacrylate, hydroxyl butyl methacrylate, allyl alcohol, glycerol methacrylate, glycidyl (meth)acrylate, allyl amine, and tert-butyl aminoethyl methacrylate.

7. The ethylenically unsaturated macromonomer according to claim 1 wherein the chain extender material is glycerol.

8. The ethylenically unsaturated macromonomer according to claim 1 wherein the molar ratio of oil:enophile:unsaturated monomer:chain extender material is 1:1.5:0.75:0.30.

9. The ethylenically unsaturated macromonomer according to claim 1, wherein the ethylenically unsaturated macromonomer has a weight average molecular weight, Mw, of from 1000 to 50000 Daltons.

10. A process of making a macromonomer comprising the steps of:
    i) reacting an unsaturated non-mineral oil with an enophile having an acid, ester or anhydride moiety, optionally in the presence of iodine, to form an adduct;

ii) reacting the adduct with an ethylenically unsaturated monomer having a moiety reactive with the acid, ester or anhydride moiety of the enophile to form an intermediate; and iii) reacting the intermediate of step ii) with a chain extender material having at least two moieties reactive with the acid, ester or anhydride of the enophile.

11. An addition polymer derived from an ethylenically unsaturated monomer composition comprising the ethylenically unsaturated macromonomer according to claim 1.

12. The addition polymer according to claim 11 wherein the addition polymer is in the form of an aqueous dispersion of polymer microparticles.

13. The addition polymer according to claim 12 wherein the microparticles have a mean average diameter of from 0.05 microns to 2.00 microns.

14. The addition polymer according to claim 12 wherein the Tg of the polymer is from −20 to 120° C.

15. A coating composition comprising the addition polymer according to claim 12.

16. The coating composition according to claim 15, further comprising ingredients selected from the group consisting of pigments, fillers, waxes, extenders, rheological modifiers, dispersants, anti-foams, tackifiers, plasticisers, flow aids and biocides.

17. The ethylenically unsaturated macromonomer according to claim 2 wherein the unsaturated non-mineral oil is selected from the group consisting of palm oil, sunflower oil, soya bean oil, safflower oil and rape seed oil.

18. The ethylenically unsaturated macromonomer according to claim 2 wherein the enophile is selected from the group consisting of maleic anhydride, itaconic anhydride, fumaric acid, acrylic acid and maleate esters.

19. The ethylenically unsaturated macromonomer according to claim 2 wherein the monomer reactive with the acid, ester or anhydride of the enophile is selected from the group consisting of hydroxyl ethyl (meth)acrylate, hydroxyl propyl (meth)acrylate, hydroxyl iso propyl methacrylate, hydroxyl butyl methacrylate, allyl alcohol, glycerol methacrylate, glycidyl (meth)acrylate, allyl amine, and tert-butyl aminoethyl methacrylate.

20. The ethylenically unsaturated macromonomer according to claim 2 wherein the molar ratio of oil:enophile:unsaturated monomer:chain extender material is 1:1.5:0.75:0.30.

* * * * *